United States Patent
Amor et al.

[11] Patent Number: 6,059,809
[45] Date of Patent: May 9, 2000

[54] PROTECTIVE ANGIOPLASTY DEVICE

[75] Inventors: Max Amor, Nancy, France; Noureddine Frid, Beersel, Belgium; Michel Henry, Nancy, France; Daniel Rufnacht, Genève, Switzerland

[73] Assignee: Medicorp, S.A., Cedex, France

[21] Appl. No.: 09/086,382

[22] Filed: May 29, 1998

[30] Foreign Application Priority Data

Feb. 16, 1998 [EP] European Pat. Off. .............. 98200476
May 4, 1998 [EP] European Pat. Off. .............. 98201420

[51] Int. Cl.$^7$ ...................................................... A61M 5/32
[52] U.S. Cl. .............................................. 606/194; 604/96
[58] Field of Search .................................... 606/108, 191, 606/192, 194, 198; 623/1, 11, 12; 604/96, 99, 912, 915, 920

[56] References Cited

U.S. PATENT DOCUMENTS

| | | |
|---|---|---|
| 4,425,908 | 1/1984 | Simon . |
| 4,503,569 | 3/1985 | Dotter . |
| 4,512,338 | 4/1985 | Balko et al. . |
| 4,580,568 | 4/1986 | Gianturco . |
| 4,655,771 | 4/1987 | Wallsten . |
| 4,665,906 | 5/1987 | Jervis . |
| 4,681,110 | 7/1987 | Wiktor . |
| 4,743,251 | 5/1988 | Barra . |
| 4,795,458 | 1/1989 | Regan . |
| 4,911,163 | 3/1990 | Fina ......................................... 606/127 |
| 4,950,227 | 8/1990 | Savin et al. . |
| 4,954,126 | 9/1990 | Wallsten . |
| 5,026,377 | 6/1991 | Burton et al. . |
| 5,037,427 | 8/1991 | Harada et al. . |
| 5,061,275 | 10/1991 | Wallsten . |
| 5,067,957 | 11/1991 | Jervis . |
| 5,190,546 | 3/1993 | Jervis . |
| 5,197,978 | 3/1993 | Hess . |
| 5,201,901 | 4/1993 | Harada et al. . |
| 5,226,913 | 7/1993 | Pinchuk . |
| 5,290,295 | 3/1994 | Querals et al. ........................... 606/108 |
| 5,320,604 | 6/1994 | Walker et al. ............................. 604/96 |
| 5,354,309 | 10/1994 | Schnepp-Pesch et al. . |
| 5,395,390 | 3/1995 | Simon . |
| 5,405,377 | 4/1995 | Cragg . |
| 5,423,742 | 6/1995 | Theron . |
| 5,439,446 | 8/1995 | Barry ......................................... 604/96 |
| 5,480,423 | 1/1996 | Ravenscroft et al. . |
| 5,514,092 | 5/1996 | Forman et al. ........................... 604/101 |
| 5,540,712 | 7/1996 | Kleshinski . |
| 5,540,713 | 7/1996 | Schnepp-Pesch et al. . |
| 5,554,181 | 9/1996 | Das . |
| 5,562,725 | 10/1996 | Schmidt et al. . |
| 5,562,728 | 10/1996 | Lazarus et al. . |

(List continued on next page.)

FOREIGN PATENT DOCUMENTS

| | | |
|---|---|---|
| 1205743 | 9/1970 | European Pat. Off. . |
| 0330376 | 8/1989 | European Pat. Off. . |
| 0744164 | 5/1996 | European Pat. Off. . |
| WO 9219310 | 11/1992 | WIPO . |
| WO 9505209 | 2/1995 | WIPO . |
| WO 9530385 | 11/1995 | WIPO . |
| WO 9531945 | 2/1996 | WIPO . |
| WO 9639955 | 12/1996 | WIPO . |
| WO 9713475 | 4/1997 | WIPO . |

Primary Examiner—Wynn Wood Coggins
Assistant Examiner—Jennifer Maynard
Attorney, Agent, or Firm—Roylance, Abrams, Berdo & Goodman, L.L.P.

[57] ABSTRACT

The present invention relates to a device for protected angioplasty, intended for the implantation of luminal endoprosthesis (or stent) in critical areas such as carotid or vertebral arteries, where protection of downstream-situated organs is highly desirable. The device comprises a central stent pusher part comprising a microcatheter bearing at its distal end an atraumatic tip, the atraumatic tip being prolonged by a tip balloon part comprising an inflatable occlusive balloon which may be inflated with a physiologically acceptable fluid at predetermined rates, a fluid-releasing section extending at the proximal the of the occlusive balloon, said releasing section being able to release the fluid from the balloon into an upstream section of the vessel when the pressure of the fluid reaches a predetermined level.

20 Claims, 6 Drawing Sheets

U.S. PATENT DOCUMENTS

| | | |
|---|---|---|
| 5,575,818 | 11/1996 | Pinchuk . |
| 5,597,378 | 1/1997 | Jervis . |
| 5,609,627 | 3/1997 | Goicoechea et al. .......... 623/1 |
| 5,630,840 | 5/1997 | Mayer . |
| 5,639,274 | 6/1997 | Fischell et al. ............ 604/96 |
| 5,643,278 | 7/1997 | Wijay . |
| 5,643,339 | 7/1997 | Kavteladze et al. . |
| 5,645,559 | 7/1997 | Hachtman et al. . |
| 5,658,894 | 8/1997 | Weisz ........................ 514/58 |
| 5,674,277 | 10/1997 | Freitag . |
| 5,741,333 | 4/1998 | Frid . |
| 5,851,210 | 12/1998 | Torossian ................. 606/108 |

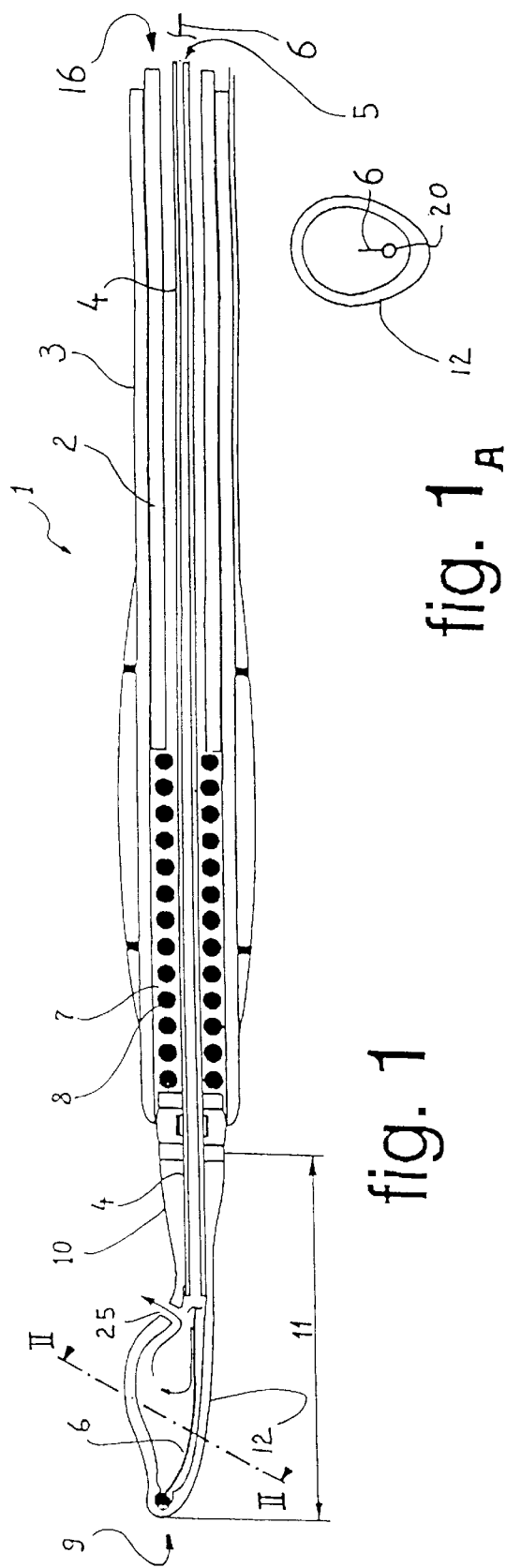
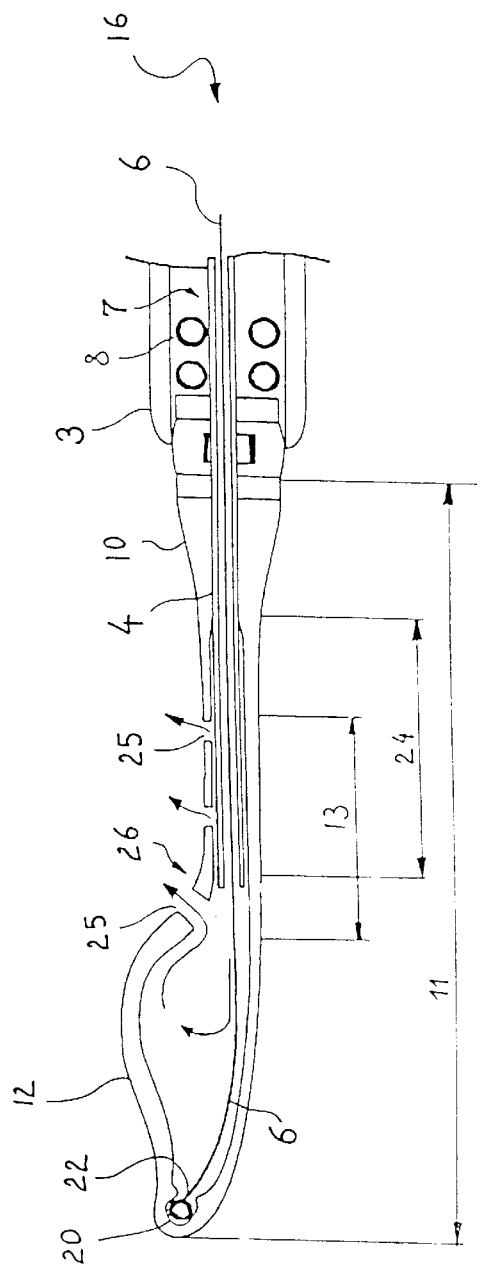

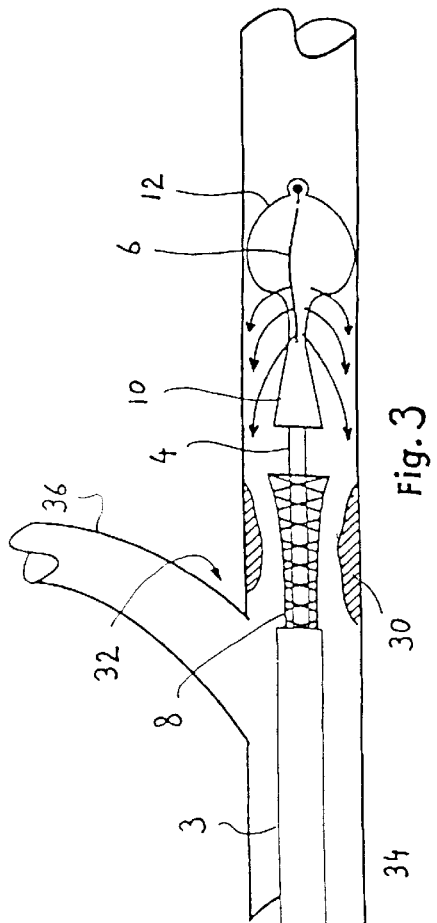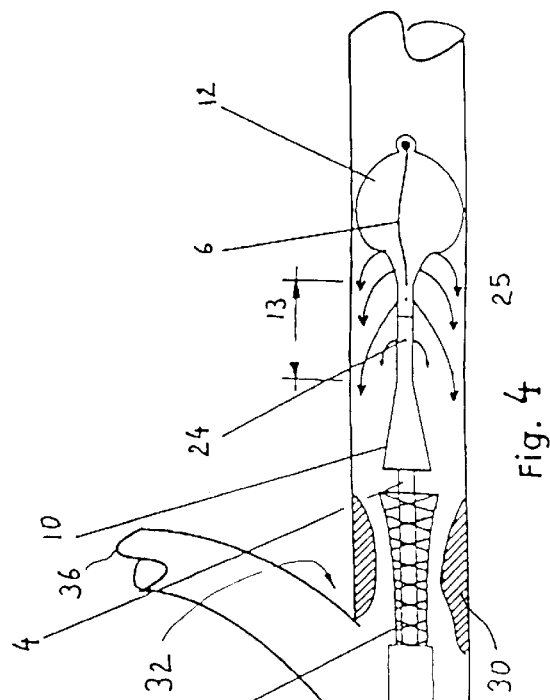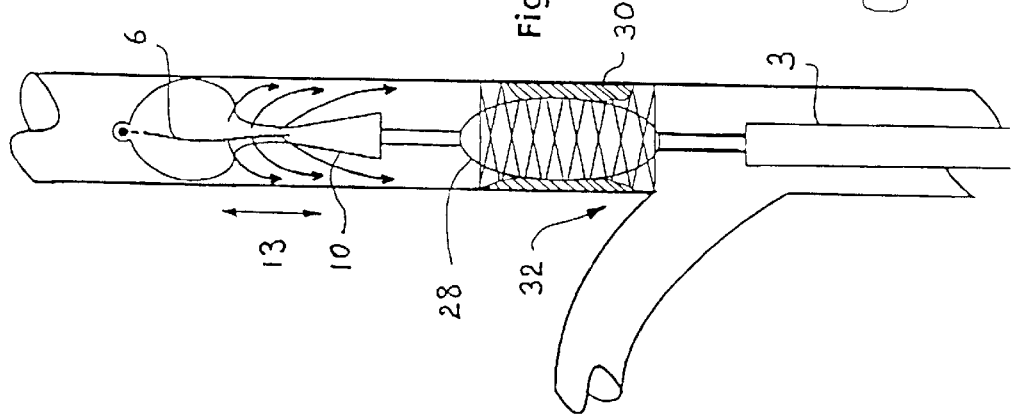

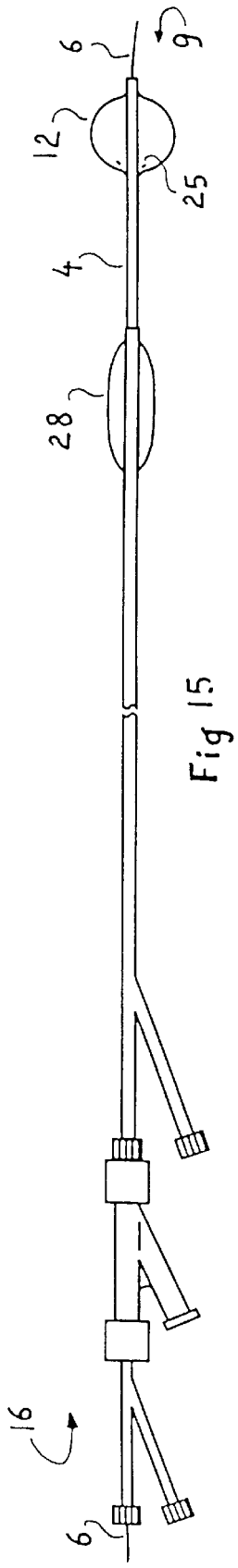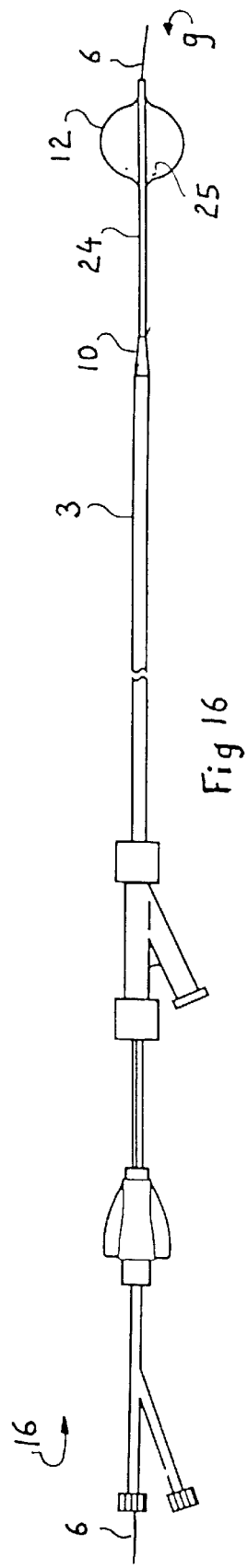

PROTECTIVE ANGIOPLASTY DEVICE

FIELD OF THE INVENTION

The present invention relates to a device for protected angioplasty, intended for the implantation of luminal endoprostheses (or stent) in critical areas such as carotid or vertebral arteries, where tempory protection of downstream-situated organs is highly desirable.

BACKGROUND OF THE INVENTION

Angioplasty is now recognized as a highly valuable method for curing stenosis and other luminal diseases of the vascular system.

However, this technique, although quite appreciated and constantly improved, is not yet systematically used for treating each type of such diseases.

In particular, the brain is a critical area, where vessels are very thin and where even short occlusions could lead to irreversible damages for the patient.

Vessels near the brain, for instance, the carotid bifurcation, should be treated with high care because incident epiphenomena that could be considered minor in other places could have disastrous consequences for the patient when present in such vessels. The circulation of blood should not be interrupted so as to avoid serious consequences, due to the lack of oxygen in the brain. It is generally understood that circulation may not be interrupted for more than a couple of minutes.

The carotid and the carotid bifurcation are furthermore, from a mechanical point of view, critical parts of the body.

The carotid bifurcation has a specific shape (including a segment of widened then restricted cross-section), which is known to provoke turbulences in the blood flow, leading to high local solicitation of the artery walls. As a consequence, stenosis problems are rather frequent in carotids.

A specific problem which occurs in treatment of stenosis in the inner carotid by angioplasty is the evacuation of debris that accumulate in the stenosis. After the stenosis is cured, the debris is naturally carried by the flowing blood. Hence, there is a strong risk that the debris can be transported downstream to the lesion into capillary arteries that they could block, causing thrombosis with catastrophic embolization.

The carotid is considered by some physicians as the last frontier for endovascular therapy. There is still at present considerable scepticism regarding angioplasty in the carotid.

DESCRIPTION OF THE PRIOR ART

It has thus proved desirable to improve this technique. Among recent improvements, methods for cerebral protection have been conceived and some of them are being developed. The "Report on 2nd Carotid Angioplasty Meeting, October 23 and 24, 1997, Polyclinique Essey-les-Nancy, France" summarizes various aspects of the present advancement of research and development in the field of carotid angioplasty.

The technique developed by Theron to cure carotid stenosis with cerebral protection consists of introducing a triple coaxial catheter in the common carotid. A microcatheter provided with a latex balloon at its tip is inserted through the guiding catheter. The lesion is located and the micro-catheter is advanced through the stenosis, after which said balloon is inflated downstream of the lesion. An angioplasty balloon (or dilatation balloon) is inflated at the level of the stenosis. Particles originating from the stenosis are aspired and flushed through the guiding catheter with heparin, the flow being diverted towards the external carotid. The placement of a stent is then performed, the angioplasty balloon is withdrawn. A new aspiration and a flush are performed once again, while the protection balloon remains inflated. The latter is thereafter deflated and, if the result seems satisfactory, the micro-catheter, the protection balloon and the guiding catheter are removed.

This method, although attractive, is unfortunately not very reliable.

Test have shown that when performing the method described above, a non-neglectible amount of debris can remain in the blood flow.

Much of the debris has too large a diameter to be efficiently destroyed by the white blood cells before reaching places in the brain where they could cause fatal thrombosis.

In fact, aspiration and flushing from upstream the protection balloon is not totally efficient, and furthermore necessitates that the tip of the catheter be positioned as close as possible to the balloon, and that the operation be carried out under severe control. This is liable to cause problems in such kinds of interventions where many other aspects (treatment of the stenosis, placement of the stent) must also be taken into account in a very short time.

It has been suggested to use another technique designated as a "double balloon technique", which would consist of occluding the carotid artery beyond the stenosis and also occluding the upper part of the common carotid artery, thus creating a dilatation chamber that could easily be aspirated and cleaned.

BRIEF DESCRIPTION OF THE INVENTION

Another method and device for safely implanting a luminal endoprosthesis in critical areas like carotid, has been developped, according to which efficient protection of organs situated downstream of a carotid stenosis may be obtained without any need for aspiring the debris of the lesion.

The invention covers a device for the implantation of expandable stents in a vascular vessel, allowing for temporary protection of downstream organs. This device comprises a central stent pusher part surrounded by a stent releasing part, said part being provided with an axial lumen, for inserting a microguide wire, and comprising a micro-catheter bearing at its distal end an atraumatic tip, and a stent loading cavity designed to contain a stent in a radially contracted state extending near the distal end of the stent pusher part.

The device according to the invention is characterized in that said atraumatic tip is prolonged by a tip balloon part comprising an inflatable occlusive balloon hermetically connected via the axial lumen to injection means able to feed said balloon with a physiologically acceptable fluid at predetermined rates, a fluid releasing section extending at the proximal side of the occlusive balloon, said releasing section being able to release the fluid from the balloon into an upstream section of the vessel when the pressure of said fluid reaches a predetermined level.

According to various embodiments, the fluid releasing section may be formed by the proximal end of the occlusive balloon, and possibly on the neck of the balloon or on a cane supporting the occlusive balloon.

Preferably, the stent is a self-expanding stent, which is maintained in place in the stent loading cavity by a surrounding shell.

The stent may also be a balloon-dilatable stent, with the stent releasing part comprising in such a case a dilatation balloon.

According to a prefered embodiment, the device comprises a dilatation balloon axially displaceable relative to the microcatheter.

The microguide wire may be anchored at the distal side of the occlusive balloon. In such an embodiment, the wire is preferably terminated by a ball inserted in a pouch provided at said distal side.

The invention also relates to a method for the implantation of endoluminal stent in a vessel comprising operations as described in the present text.

Thanks to this method, the debris of the stenosis are flushed away in a very efficient manner and further deviated to other places of the body where they can provoke no harm, (for instance via the outer carotid in the case where carotid stenosis is cured).

BRIEF DESCRIPTION OF THE DRAWINGS

Other advantages of the device and of the method according to the invention will appear from the description hereafter of particular embodiments thereof, reference being made to the appended drawings wherein FIG. 1 is a diagrammatic lateral view of a longitudinal cross-section of the distal end of a device according to the invention bearing a self-expanding endoprosthesis, FIG. 1a is a cross section according to line II—II of the device of FIG. 1, FIG. 2 is a detailed view of the tip and of a distal end of the device of FIG. 1, FIG. 3 is a diagrammatic lateral view in situ of a device according to FIG. 1, FIGS. 4 and 5 are diagrammatic lateral views of different embodiments of a device of the invention, FIG. 15 is a lateral view of another embodiment of the device of the invention, FIG. 16 is a lateral view of still another embodiment of the invention.

DETAILED DESCRIPTION OF THE DRAWINGS

Figure 8:
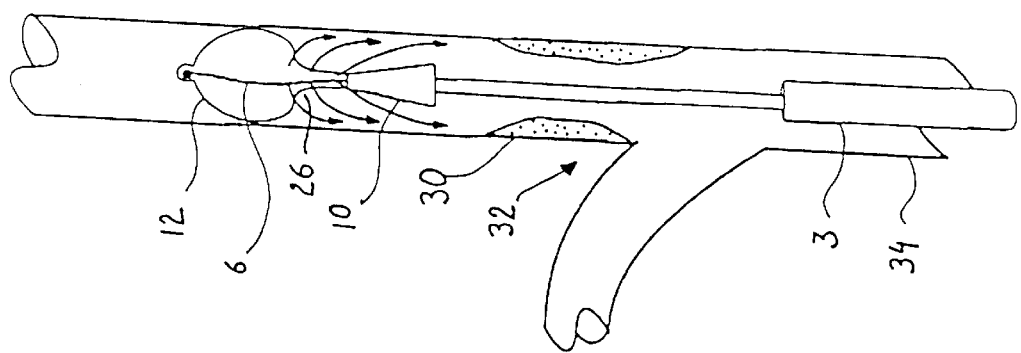
FIGS. 6 to 12 are diagrammatic views illustrating various steps of a method for using the device of the invention.
Figure 7:
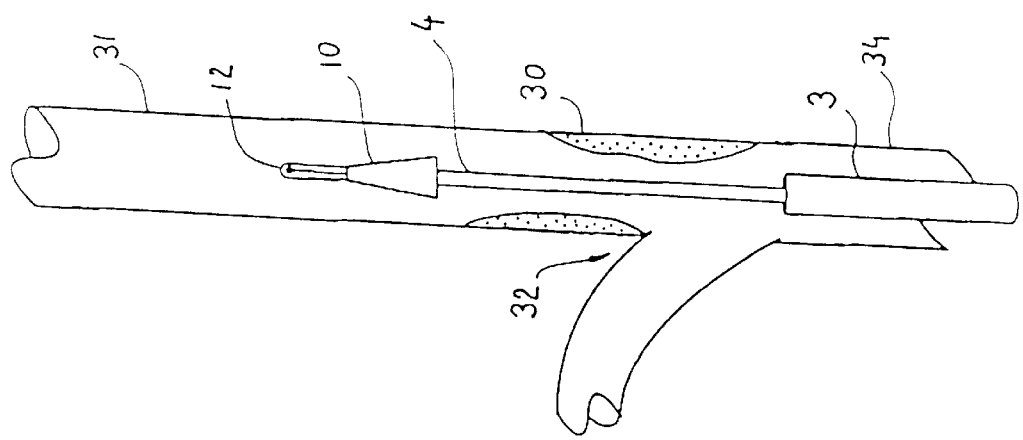
Figure 6:
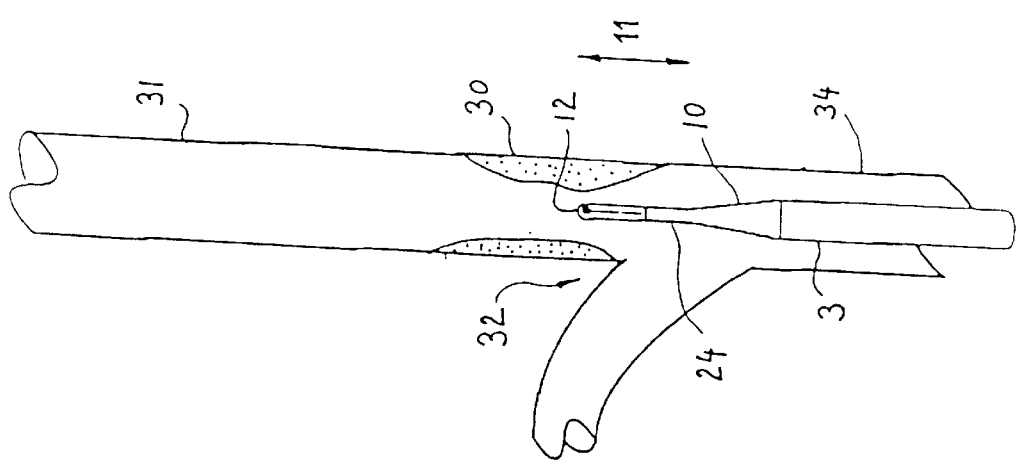
Figure 11:
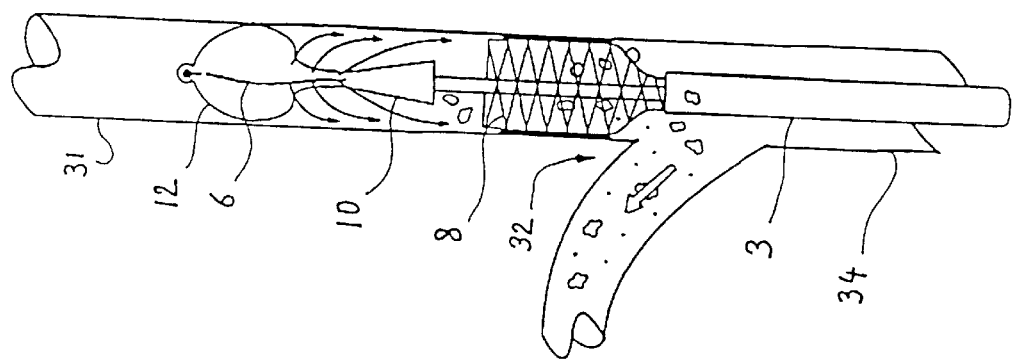
Figure 10:
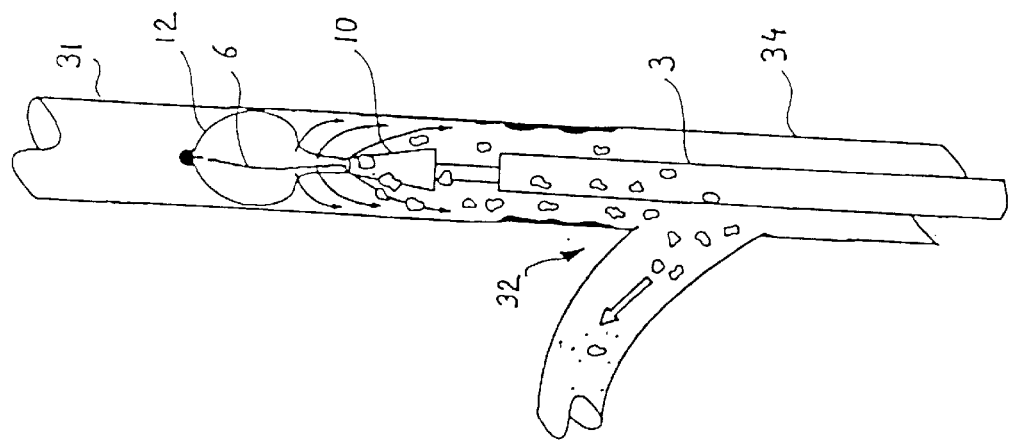
Figure 9:
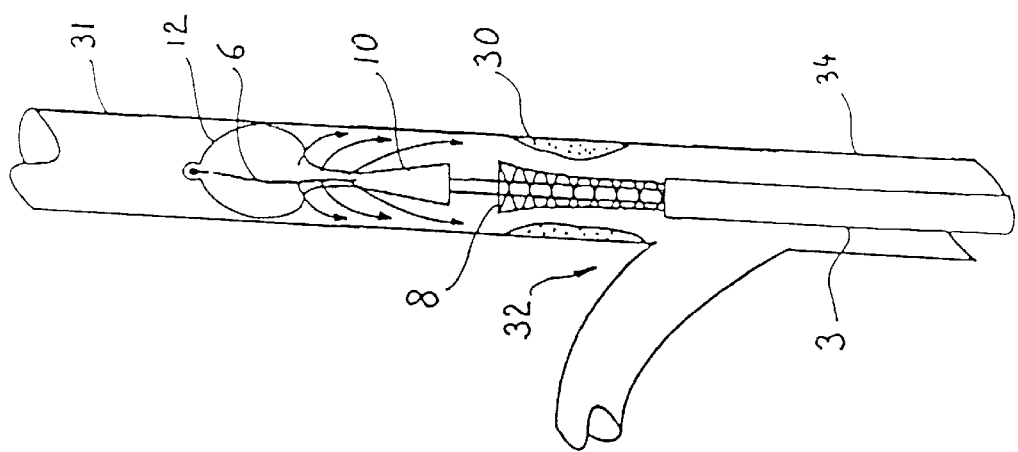
Figure 14:
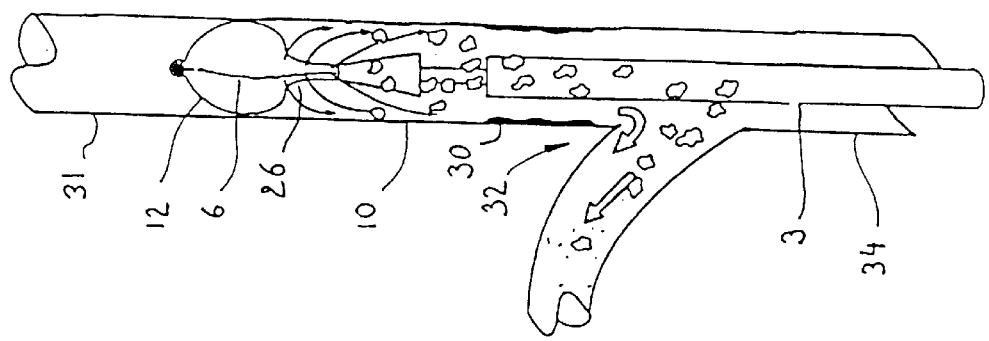
FIGS. 13 and 14 illustrate optional steps of the above method.

In the present context, the term "stent" is used for the sake of facility to define generally speaking a luminal endoprosthesis, bearing in mind that luminal endoprostheses include stents sensu stricto but can comprise, together with their framework, various kinds of coating (not shown). It is clear that the invention also relates to devices and methods where such coated stents are used.

As can be seen from FIG. 1, the device 1 according to the invention includes a central stent pusher part 2 surrounded by a stent releasing part 3.

The stent pusher part 2 comprises a microcatheter 4 provided with an axial lumen 5. A microguide wire 6 extends along the axial lumen 5. A stent loading cavity 7 able to contain a stent 8—in the present case, a self-expanding stent—is provided near the distal end 9 of the stent pusher part 2.

The distal end 9 of the device 1 bears an atraumatic tip 10 which is prolonged by a tip balloon part 11 comprising an inflatable occlusive balloon 12 and a fluid releasing section 13. The tip balloon part 11 is connected via the axial lumen 5 and a Y-adapter (not shown) to injection means placed towards the proximal end 16 of the device 1.

This injection means are able to provide a continuous flow of a physiologically acceptable fluid at a predetermined rate. A stop-lock part serves to lock the stent pusher part 2 in a fixed relative position with respect to the stent releasing part 3.

When the device 1 is inserted in a body, the tip balloon part 11 leads the device 1 through the vascular system and through possible stenoses. Indeed, it is possible to change the shape of the occlusive balloon 12 when it is in the deflated state by advancing the microguide wire 6 more or less into the tip balloon part 11.

To this end, the guide wire 6 is anchored into a tip pouch 20 of the balloon 12 by a small spherical ball 22. Relative advancement of the microguide wire 6 will therefore induce bending of the wire tip.

A marker (for instance a colour marker) at the proximal side of the guide wire 6 permits a control of the maximal allowed advancement in relation to the position of the Y-adapter on the stent pusher part 2.

The tip balloon part 11 of the device 1 serves as a barrier which prevents plaque debris from embolizing the cerebral arterial circulation, by temporarily occluding the main arterial axis (i.e. the carotid artery or the vertebral artery) upstream with respect to the lesion to be cured.

The occlusive balloon 12 can be inflated to a diameter of about 5–6 mm and at a length of about 10–12 mm, thus hermetically closing the artery while avoiding over distension thereof.

The presence of a fluid-releasing section 13 on the proximal face of the balloon 12—or just there behind—provides for an efficient flushing action represented by tiny arrows on the figures), far from the limited possibilities of classical methods.

The inflation of the occlusive balloon 12 occurs independent of the flushing function at a pressure range of approximatively 300–800 mm Hg. Flushing of the section of artery upstream from the occlusive balloon 12 occurs at increased pressures, allowing overflow fluid to escape through the fluid-releasing section 13 in the balloon neck area at a flow rate sufficient to force back the blood, possibly laden with particles, up to an upstream vascular bifurcation. The flow rate can be about 1–2 $cm^2$/sec.

This flush action causes a continuous cleaning of the vascular volume in the artery upstream from the occlusive balloon 12 whenever the balloon pressure reaches a given value, thus activating a controlled leak via the fluid-releasing section 13.

The tip balloon part 11 can be adjacent the atraumatic tip 10, as shown on FIG. 1, or placed at the tip of a cane 24 protruding from this atraumatic tip 10, as represented on FIGS. 2 and 4.

FIGS. 3 and 4 display various embodiments of the fluid-releasing section 13, the occlusion balloon 12 having been inflated by an increase of the pressure released by injection means. The fluid begins to escape from the balloon 12 at a predetermined rate through calibrated pin-holes 25 provided at the proximal side of the occlusive balloon 12 and/or of the neck 26 thereof.

The holes are preferably designed so that the fluid cannot escape unless the pressure reaches a trigger value.

The fluid-releasing section 13 can also extend on the cane 24 as shown on FIG. 4.

Of course, the device can also be guided in a conventional manner along the microguide wire 6 as can be seen on FIG. 15.

FIG. 15 further displays the proximal end of the device and various Y-adapters for connecting i.e. the axial lumens 5 to the injection means. In this case, the axial lumen 5 extends through the tip pouch 20 and comprises a separated channel to feed the tip balloon 12.

The stent releasing part 3 can be designed so as to accommodate a self-expanding stent as shown for instance in FIGS. 2 and 3 or a balloon-expandable stent, as shown in FIG. 5; in this case, the stent-releasing part includes a dilatation balloon 28.

FIGS. 6 to 12 illustrate diagrammatically the various steps of the safe method according to the invention which may now be applied by using the above-described device 1 according to the invention.

When the distal end 9 of the device 1 has been inserted in the vascular system according to a known method (generally from the femoral artery), it is driven easily up to the site to be cured, which in the present case a stenosis 30 in the inner carotid 31, downstream with respect to the bifurcation 32 of the common carotid 34.

The microcatheter 4 is then extended up to a segment of the inner carotid 31 beyond the stenosis 30. The injection means are then activated, at a predetermined rate, so that the pressure of the fluid increases in the axial lumen 5, thereby causing the balloon 12 to expand.

When the balloon 12 reaches a diameter substantially equal to that of the inner carotid 31, its internal pressure begins to rise, causing the pin-holes 25 of the fluid-releasing section 13 to open and, flushing backwards the fluid and the blood volume trapped behind the balloon 12. The brain is therefore protected from particles liable to escape from the stenosis 30, and the physician can immediately begin to proceed with placement of a stent 8, which can be either a self-expanding stent 8 constricted in the stent loading area 7, or a balloon-expandable stent. In the latter case, the placement implies activating a dilatation balloon 28 as can be seen in FIG. 5.

During this operation, the tip balloon part 11 goes on flushing backwards the blood laden with particles up to the carotic bifurcation 32, with this laden blood being diverted through the outer carotid 36 to other organs where it can cause no harm.

It should be stressed that debris and particles are completely flushed away, since there remains no place behind the balloon 12 where they could stay.

Figure 13:
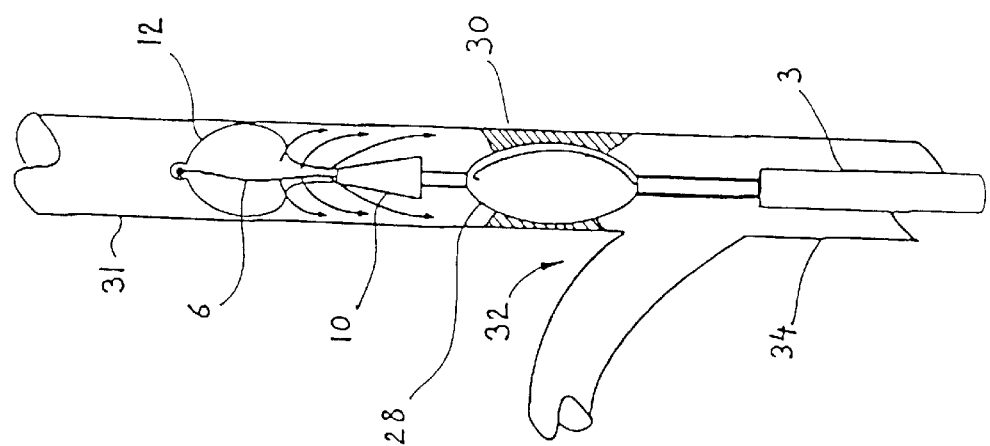
Figure 12:
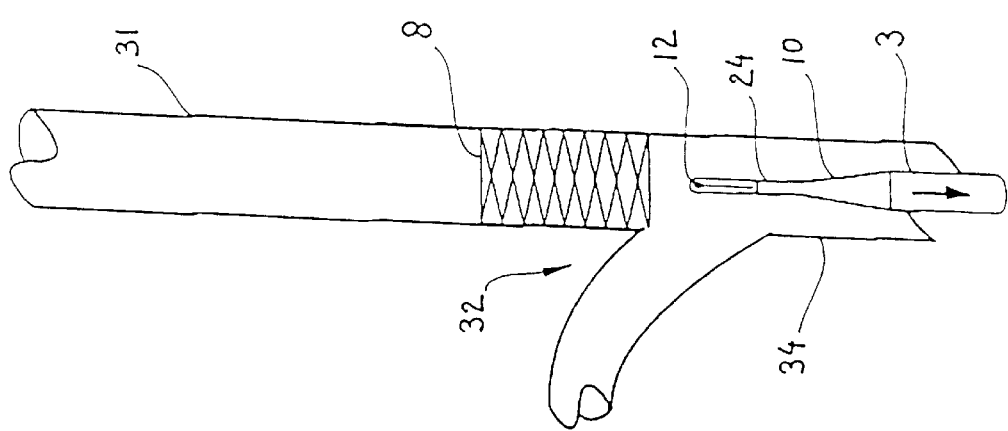

If necessary, depending on the state of the stenosis 30, it is possible to proceed within the allowed time, prior to the insertion of the stent 8, as shown in FIG. 13, to widen of the section to be cured, while allowing plaque debris to be still carried away by the constant flushing of the artery.

Another feature of the present device becomes apparent when comparing FIG. 4 and FIG. 13: the dilatation balloon 28 shown in the latter is able to slide along the microcatheter 4 and can accordingly reach at will any part of the artery wall to be cured upstream from the occlusive balloon 12. To allow such an axial displacement, the balloon 28 is connected to a balloon pusher, placed between the microcatheter 4 and the stent releasing part 3.

During the whole operation, the duly monitored injection means go on feeding the occlusive balloon 12 and the fluid-releasing section 13 at a rate sufficient to keep the balloon 12 safely inflated and to provide a sufficient flow rate to drive the blood to the bifurcation 32.

When the operation is complete, the balloon 12 can be instantaneously deflated and withdrawn through the implanted stent 8.

The stent-releasing part 3 may comprise an outer tubing or, to reduce the diameter, a single outer tubing making it possible to directly release the stent 8 at its predetermined place.

Advantageously, the outer tubing can comprise radio-visible markers allowing the stent 8 to be placed accurately at its required place.

An advantage of the device of the invention is that, once the occlusive balloon 12 has been placed, it is possible, depending on the circumstances, to carry out without delay a wide variety of operations on the site to be cured. If necessary, it is even possible, in a matter of seconds, to replace a part of the device without disturbing the blocking function of the tip part. The time spared can make the difference for the patient.

The device can be also provided as a kit of parts to be assembled, which allows the operator to select and assemble, for example at the very moment of the operation, the kind of stent he feels to be the more adapted to the circumstances and the corresponding stent releasing part.

FIG. 16 displays another embodiment of the device, which in the present case includes a tip balloon part 11 and a dilatation balloon 28 axially displaceable relative to same, but devoid of stent relasing part 3.

The embodiment of the device shown in FIG. 16 can either be used as such in particular cases wherein it is not compulsory to place a stent after having cured the stenosis or as part of a kit, to perform the preliminary operations of an intervention, bearing in mind that an adequate stent releasing part can be fitted thereon within a few seconds without interrupting the blocking action of the occlusive balloon 12.

What is claimed is:

1. A device for the implantation of expandable stents in a vascular vessel, allowing for temporary protection of downstream organs, comprising:

a central stent pusher part surrounded by a stent-releasing part, said central stent pusher part being provided with an axial lumen bearing at its distal end an atraumatic tip, a stent loading cavity designed to contain a stent in a radially contracted state extending near the distal end of the stent pusher part, wherein said atraumatic tip is prolonged by a tip balloon part comprising an inflatable occlusive balloon hermetically connected via the axial lumen to an injector adapted to feed said balloon with a physiologically acceptable fluid at predetermined rates, and a fluid-releasing section extends at a proximal side of the occlusive balloon, said releasing section being able to release the fluid from the balloon into an upstream section of the vessel when the pressure of said fluid reaches a predetermined level.

2. A device according to claim 1, wherein the fluid-releasing section extends at a proximal end of the proximal side of the occlusive balloon.

3. A device according to claim 1, wherein the occlusive balloon has a neck, and the fluid-releasing section extends on the neck of the balloon.

4. A device according to claim 2, wherein the occlusive balloon has a neck, and the fluid-releasing section extends on the neck of the balloon.

5. A device according to claim 2, wherein the fluid-releasing section further extends on a cane supporting the occlusive balloon.

6. A device according to claim 4, wherein the fluid-releasing section further extends on a cane supporting the occlusive balloon.

7. A device according to claim 1, comprising a self-expanding stent, which is maintained in place in the stent loading cavity by a surrounding shell.

8. A device according to claim 1, comprising a balloon-dilatable stent, the stent-releasing part comprising a dilatation balloon.

9. A device according to claims 1 which comprises a dilatation balloon axially displaceable relative to the microcatheter.

10. A device according to claims 7 which comprises a dilatation balloon axially displaceable relative to the microcatheter.

11. A device according to claims 8 which comprises a dilatation balloon axially displaceable relative to the microcatheter.

12. A device for the implantation of expandable stents in a vascular vessel, allowing for temporary protection of downstream organs, comprising:
 a central stent pusher part surrounded by a stent-releasing part, said central pusher part being provided with an axial lumen bearing at its distal end an atraumatic tip,
 a stent loading cavity designed to contain a stent in a radially contracted state extending near the distal end of the stent pusher part, and
 a microguide wires,
 wherein
  the atraumatic tip is prolonged by a tip balloon part comprising an inflatable occlusive balloon hermetically connected via the axial lumen to an injector adapted to feed said balloon with a physiologically acceptable fluid at predetermined rates,
  a fluid-releasing section extends at the proximal side of the occlusive balloon, said releasing section being able to release the fluid from the balloon into an upstream section of the vessel when the pressure of said fluid reaches a predetermined level, and
  the microguide wire is anchored at a distal side of the occlusive balloon.

13. A device according to claim 12, wherein the wire is terminated by a ball inserted in a pouch provided at said distal side.

14. A device for performing angioplasty in a vascular vessel, allowing for temporary protection of downstream organs, comprising:
 a central pusher part provided with an axial lumen, bearing at its distal end a tip balloon part comprising an inflatable occlusive balloon hermetically connected via the axial lumen to an injector adapted to feed said balloon with a physiologically acceptable fluid at predetermined rates,
 a fluid-releasing section extending at a proximal side of the occlusive balloon, said releasing section being able to release the fluid from the balloon into an upstream section of the vessel when the pressure of said fluid reaches a predetermined level, and
 a dilatation balloon axially displaceable relative to the tip balloon.

15. A device according to claim 14, wherein the fluid-releasing section extends at a proximal end of the occlusive balloon.

16. A device according to claim 15, wherein the occlusive balloon has a neck, and the fluid-releasing section extends on the neck of the balloon.

17. A device according to claim 16, wherein the fluid-releasing section further extends on a cane supporting the occlusive balloon.

18. A device according to claim 14, provided, toward its proximal end, with connection means for inserting a stent-relasing part while the tip balloon is inflated.

19. A device according to claim 1, wherein said injector is adapted to feed said balloon with said physiologically acceptable fluid said predetermined rates so that said releasing section releases said fluid into said upstream section at a rate sufficient to move debris in said upstream section.

20. A device according to claim 14, wherein said injector means is adapted to feed said balloon with said physiologically acceptable fluid said predetermined rates so that said releasing section releases said fluid into said upstream section at a rate sufficient to move debris in said upstream section.

* * * * *